United States Patent
Igarashi et al.

(10) Patent No.: US 10,631,720 B2
(45) Date of Patent: Apr. 28, 2020

(54) BIOLOGICAL OBSERVATION AND LIGHT COLOR COMPONENT SEPARATION SYSTEM

(71) Applicant: OLYMPUS CORPORATION, Tokyo (JP)

(72) Inventors: Makoto Igarashi, Hachioji-shi (JP); Kenji Yamazaki, Hino-shi (JP); Kotaro Ogasawara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 315 days.

(21) Appl. No.: 15/705,458

(22) Filed: Sep. 15, 2017

(65) Prior Publication Data
US 2018/0000335 A1    Jan. 4, 2018

Related U.S. Application Data

(63) Continuation of application No. PCT/JP2015/074964, filed on Sep. 2, 2015.

(30) Foreign Application Priority Data

Mar. 17, 2015  (JP) ................. 2015-053689

(51) Int. Cl.
*A61B 1/06* (2006.01)
*A61B 1/04* (2006.01)
(Continued)

(52) U.S. Cl.
CPC ........ *A61B 1/0638* (2013.01); *A61B 1/00009* (2013.01); *A61B 1/00045* (2013.01);
(Continued)

(58) Field of Classification Search
CPC combination set(s) only.
See application file for complete search history.

(56) References Cited

U.S. PATENT DOCUMENTS

2003/0176768 A1* 9/2003 Gono ................... A61B 1/0638
                                                           600/109
2005/0010081 A1* 1/2005 Doguchi ............ A61B 1/00009
                                                           600/109
(Continued)

FOREIGN PATENT DOCUMENTS

EP   2 604 170 A1   6/2013
EP   2896354 A1    7/2015
(Continued)

OTHER PUBLICATIONS

International Search Report dated Dec. 1, 2015 issued in PCT/JP2015/074964.
(Continued)

*Primary Examiner* — John P Leubecker
*Assistant Examiner* — Shankar Raj Ghimire
(74) *Attorney, Agent, or Firm* — Scully, Scott, Murphy & Presser, P.C.

(57) ABSTRACT

A biological observation system includes: a light source apparatus configured to supply a first illuminating light, and a second illuminating light, while switching between the first illuminating light and the second illuminating light; an image pickup device configured to receive light from an object at each of a plurality of pixels having different sensitivities, and picks up an image; a color separation processing portion configured to separate, from respective color components, a color component obtained when an image of light of a predetermined wavelength band is picked up by a pixel having the greatest sensitivity to the light in the predetermined wavelength band; and a control portion configured to cause different processing to be performed between a case where an inputted image pickup signal corresponds to the first illuminating light and a case where
(Continued)

an inputted image pickup signal corresponds to the second illuminating light.

8 Claims, 2 Drawing Sheets

(51) Int. Cl.
  *G02B 23/24* (2006.01)
  *H04N 5/235* (2006.01)
  *H04N 9/04* (2006.01)
  *A61B 1/00* (2006.01)
  *H04N 5/225* (2006.01)
  *H04N 5/243* (2006.01)
  *H04N 9/64* (2006.01)

(52) U.S. Cl.
  CPC .............. *A61B 1/04* (2013.01); *A61B 1/0646* (2013.01); *G02B 23/2469* (2013.01); *H04N 5/2256* (2013.01); *H04N 5/2354* (2013.01); *H04N 5/243* (2013.01); *H04N 9/04557* (2018.08); *H04N 9/64* (2013.01); *G02B 23/2484* (2013.01); *H04N 2005/2255* (2013.01)

(56) References Cited

U.S. PATENT DOCUMENTS

| | | | | |
|---|---|---|---|---|
| 2007/0078299 | A1* | 4/2007 | Ayame | A61B 1/00186 600/101 |
| 2007/0153542 | A1* | 7/2007 | Gono | A61B 1/0638 362/574 |
| 2007/0276185 | A1* | 11/2007 | Gono | A61B 1/0008 600/156 |
| 2009/0066787 | A1* | 3/2009 | Yamazaki | A61B 1/0638 348/70 |
| 2011/0115882 | A1* | 5/2011 | Shahinian | A61B 1/00193 348/45 |
| 2012/0253157 | A1* | 10/2012 | Yamaguchi | A61B 1/0638 600/328 |
| 2013/0012794 | A1* | 1/2013 | Zeng | A61B 1/00186 600/328 |
| 2013/0018242 | A1* | 1/2013 | Yamaguchi | A61B 1/0638 600/339 |
| 2013/0293693 | A1* | 11/2013 | Igarashi | A61B 1/00009 348/70 |
| 2013/0329027 | A1* | 12/2013 | Igarashi | A61B 1/06 348/68 |
| 2015/0022647 | A1 | 1/2015 | Takei et al. | |

FOREIGN PATENT DOCUMENTS

| | | |
|---|---|---|
| JP | 2000-262459 A | 9/2000 |
| JP | 2005-152366 A | 6/2005 |
| JP | 2011-092690 A | 5/2011 |
| JP | 2014-050595 | 3/2014 |
| WO | WO 2014/125724 A1 | 8/2014 |

OTHER PUBLICATIONS

Extended Supplementary European Search Report dated Mar. 6, 2019 in European Patent Application 15 88 5530.4.

* cited by examiner

BIOLOGICAL OBSERVATION AND LIGHT COLOR COMPONENT SEPARATION SYSTEM

CROSS REFERENCE TO RELATED APPLICATION

This application is a continuation application of PCT/JP2015/074964 filed on Sep. 2, 2015 and claims benefit of Japanese Application No. 2015-053689 filed in Japan on Mar. 17, 2015, the entire contents of which are incorporated herein by this reference.

BACKGROUND OF THE INVENTION

1. Field of the Invention

The present invention relates to a biological observation system, and more particularly to a biological observation system for observing living tissue inside a body cavity.

2. Description of the Related Art

Among observation apparatuses or observation systems for observing living tissue inside a body cavity using an endoscope or the like, apparatuses and systems are known that enable selection of a desired observation mode among a plurality of observation modes, for example, an observation mode that displays an image of living tissue with similar color tones to the color tones when viewing living tissue with a naked eye, an observation mode that displays an image of living tissue so as to emphasize capillary vessels that are present in a surface layer of living tissue, and an observation mode that displays an image of living tissue so as to emphasize blood vessels with a large diameter that are present at a deep part of living tissue.

Specifically, for example, in Japanese Patent Application Laid-Open Publication No. 2014-50595 a configuration is disclosed that, in an endoscope apparatus in which a rotary filter configured to perform wavelength separation with respect to broad-band light emitted from a white light source to separate the broad-band light into light of predetermined wavelengths is provided inside a light source apparatus, enables selection of a desired mode from among a normal mode that displays a normal image in accordance with B light, G light and R light that are generated when a first filter region of the rotary filter is set on the optical path of the broad-band light, a first special mode that displays a first narrow-band image in accordance with Bn light and Gn light that are generated when a second filter region of the rotary filter is set on the optical path of the broad-band light, and a second special mode that displays a second narrow-band image in accordance with the Bn light, the Gn light and oxygen saturation measuring light that are generated when a third filter region of the rotary filter is set on the optical path of the broad-band light.

SUMMARY OF THE INVENTION

A biological observation system comprising:
a light source apparatus configured to, as illuminating light for illuminating an object, supply a first red light having a wavelength band belonging to a red region and light having a wavelength band belonging to a region other than the red region as a first illuminating light, and supply a second red light having a wavelength band belonging to the red region and having an absorption coefficient for blood that is lower than an absorption coefficient for blood of the first red light, and light having a wavelength band belonging to a region other than the red region as a second illuminating light, and to supply the first illuminating light and the second illuminating light at mutually different timings while switching between the first illuminating light and the second illuminating light;
an image pickup device comprising a plurality of pixels having spectral sensitivities such that a sensitivity to any one color among a predetermined plurality of colors is relatively higher than a sensitivity to other colors than the one color, and which is configured to receive light from an object and generate an image pickup signal for each of the plurality of pixels; and
a processor comprising hardware, wherein the processor is configured to:
   perform color separation processing for separating, from an image pickup signal generated by the image pickup device, an image pickup signal corresponding to a color component obtained when an image of light of a predetermined wavelength band included in light from the object is picked up by a pixel having a greatest sensitivity to the light of the predetermined wavelength band among the plurality of pixels; and
   in a case where an image pickup signal that is inputted to the processor is an image pickup signal corresponding to the first illuminating light, perform a first color separation processing that separates the image pickup signal into a signal corresponding to the first red light and a signal corresponding to light belonging to a region other than the red region, and in a case where an image pickup signal that is further inputted to the processor is an image pickup signal corresponding to the second illuminating light, switch to a second color separation processing that separates the image pickup signal into a signal corresponding to the second red light and a signal corresponding to light belonging to a region other than the red region,
wherein as light belonging to a region other than the red region, the light source apparatus supplies at least one light among a first blue light, a second blue light having an absorption coefficient for blood that is lower than an absorption coefficient for blood of the first blue light, and a green light,
wherein the image pickup device comprises:
   a first pixel having a spectral sensitivity such that, among three colors of red, green and blue, a sensitivity to red is relatively higher than a sensitivity to colors other than red;
   a second pixel having a spectral sensitivity such that, among the three colors, a sensitivity to green is relatively higher than a sensitivity to colors other than green; and
   a third pixel having a spectral sensitivity such that, among the three colors, a sensitivity to blue is relatively higher than a sensitivity to colors other than blue,
wherein the light source apparatus is configured to supply the first blue light, the second blue light, the green light, the first red light and the second red light, and to supply the first red light and the second blue light as the first illuminating light and to supply the second red light and the second blue light as the second illuminating light, and wherein the processor is configured to cause processing for separating, from an image pickup signal generated by the image pickup device, a red color component obtained by picking up an image of the first red light that is included in light from the object at the first pixel, and a blue color component obtained by picking up an image of the second blue light that is included in light from the object at the third pixel to be performed as the first color separation processing, and to cause processing for separating, from an image pickup signal generated by the image pickup device, a red color component obtained by picking up an image of the second red light that is included in light from the object at the first pixel, and a blue color component obtained by picking up an image of the second blue light that is included in light from the object at the third pixel to be performed as the second color separation processing.

A biological observation system comprising:
a light source apparatus configured to, as illuminating light for illuminating an object, supply a first red light having a wavelength band belonging to a red region and light having a wavelength band belonging to a region other than the red region as a first illuminating light, and supply a second red light having a wavelength band belonging to the red region and having an absorption coefficient for blood that is lower than an absorption coefficient for blood of the first red light, and light having a wavelength band belonging to a region other than the red region as a second illuminating light, and to supply the first illuminating light and the second illuminating light at mutually different timings while switching between the first illuminating light and the second illuminating light;
an image pickup device comprising a plurality of pixels having spectral sensitivities such that a sensitivity to any one color among a predetermined plurality of colors is relatively higher than a sensitivity to other colors than the one color, and which is configured to receive light from an object and generate an image pickup signal for each of the plurality of pixels; and
a processor comprising hardware, wherein the processor is configured to:
perform color separation processing for separating, from an image pickup signal generated by the image pickup device, an image pickup signal corresponding to a color component obtained when an image of light of a predetermined wavelength band included in light from the object is picked up by a pixel having a greatest sensitivity to the light of the predetermined wavelength band among the plurality of pixels; and
in a case where an image pickup signal that is inputted to the processor is an image pickup signal corresponding to the first illuminating light, perform a first color separation processing that separates the image pickup signal into a signal corresponding to the first red light and a signal corresponding to light belonging to a region other than the red region, and in a case where an image pickup signal that is further inputted to the processor is an image pickup signal corresponding to the second illuminating light, switch to a second color separation processing that separates the image pickup signal into a signal corresponding to the second red light and a signal corresponding to light belonging to a region other than the red region,
wherein as light belonging to a region other than the red region, the light source apparatus supplies at least one light among a first blue light, a second blue light having an absorption coefficient for blood that is lower than an absorption coefficient for blood of the first blue light, and a green light,
wherein the image pickup device comprises:
a first pixel having a spectral sensitivity such that, among three colors of red, green and blue, a sensitivity to red is relatively higher than a sensitivity to colors other than red;
a second pixel having a spectral sensitivity such that, among the three colors, a sensitivity to green is relatively higher than a sensitivity to colors other than green; and
a third pixel having a spectral sensitivity such that, among the three colors, a sensitivity to blue is relatively higher than a sensitivity to colors other than blue,
wherein the light source apparatus is configured to supply the first blue light, the second blue light, the green light, the first red light and the second red light, and supply the first red light and the second blue light as the first illuminating light and supply the second red light and the green light as the second illuminating light, and
wherein the processor is configured to cause a first color separation processing for separating, from an image pickup signal generated by the image pickup device, a red color component obtained by picking up an image of the first red light that is included in light from the object at the first pixel, and a blue color component obtained by picking up an image of the second blue light that is included in light from the object at the third pixel to be performed, and to cause a second color separation processing for separating, from an image pickup signal generated by the image pickup device, a red color component obtained by picking up an image of the second red light that is included in light from the object at the first pixel, and a green color component obtained by picking up an image of the green light that is included in light from the object at the second pixel to be performed.

A biological observation system comprising:
a light source apparatus configured to, as illuminating light for illuminating an object, supply a first red light having a wavelength band belonging to a red region and light having a wavelength band belonging to a region other than the red region as a first illuminating light, and supply a second red light having a wavelength band belonging to the red region and having an absorption coefficient for blood that is lower than an absorption coefficient for blood of the first red light, and light having a wavelength band belonging to a region other than the red region as a second illuminating light, and to supply the first illuminating light and the second illuminating light at mutually different timings while switching between the first illuminating light and the second illuminating light;
an image pickup device comprising a plurality of pixels having spectral sensitivities such that a sensitivity to any one color among a predetermined plurality of colors is relatively higher than a sensitivity to other colors than the one color, and which is configured to receive light from an object and generate an image pickup signal for each of the plurality of pixels; and
a processor comprising hardware, wherein the processor is configured to:
perform color separation processing for separating, from an image pickup signal generated by the image pickup device, an image pickup signal corresponding to a color component obtained when an image of light of a predetermined wavelength band included in light from the object is picked up by a pixel having a greatest sensitivity to the light of the predetermined wavelength band among the plurality of pixels; and in a case where an image pickup signal that is inputted to the processor is an image pickup signal corresponding to the first illuminating light, perform a first color separation processing that separates the image pickup signal into a signal corresponding to the first red light and a signal corresponding to light belonging to a region other than the red region, and in a case where an image pickup signal that is further inputted to the processor is an image pickup signal corresponding to the second illuminating light, switch to a second color separation processing that separates the image pickup signal into a signal corresponding to the second red light and a signal corresponding to light belonging to a region other than the red region, wherein as light belonging to a region other than the red region, the light source apparatus supplies at least one light among a first blue light, a second blue light having an absorption coefficient for blood that is lower than an absorption coefficient for blood of the first blue light, and a green light, wherein the image pickup device comprises:
  a first pixel having a spectral sensitivity such that, among three colors of red, green and blue, a sensitivity to red is relatively higher than a sensitivity to colors other than red;
  a second pixel having a spectral sensitivity such that, among the three colors, a sensitivity to green is relatively higher than a sensitivity to colors other than green; and
  a third pixel having a spectral sensitivity such that, among the three colors, a sensitivity to blue is relatively higher than a sensitivity to colors other than blue, wherein the light source apparatus is configured to supply the first red light and the second blue light as the first illuminating light, and to supply the second red light, the first blue light and the green light as the second illuminating light, and wherein the processor is configured to cause processing for separating, from an image pickup signal generated by the image pickup device, a color component obtained by picking up an image of the first red light that is included in light from the object at the first pixel, and a color component obtained by picking up an image of the second blue light that is included in light from the object at the third pixel to be performed as the first color separation processing, and to cause processing for separating, from an image pickup signal generated by the image pickup device, a color component obtained by picking up an image of the second red light that is included in light from the object at the first pixel, a color component obtained by picking up an image of the green light that is included in light from the object at the second pixel, and a color component obtained by picking up an image of the first blue light that is included in light from the object at the third pixel to be performed as the second color separation processing.

DETAILED DESCRIPTION OF THE PREFERRED EMBODIMENT(S)

Hereunder, an embodiment of the present invention is described while referring to the accompanying drawings.

Figure 1:
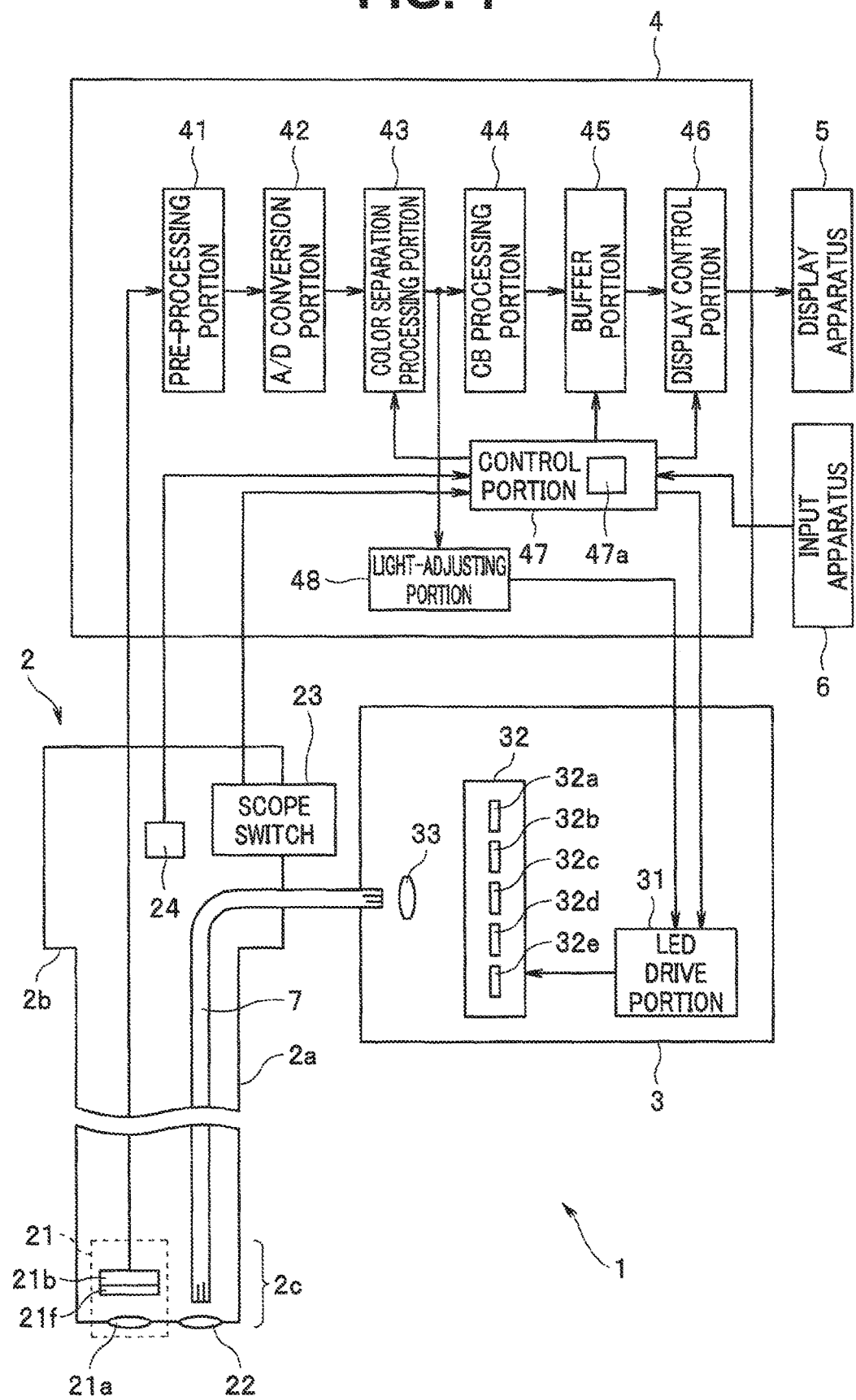
FIG. 1 is a view illustrating a configuration of main components of a biological observation system according to an embodiment of the present invention.
Figure 2:
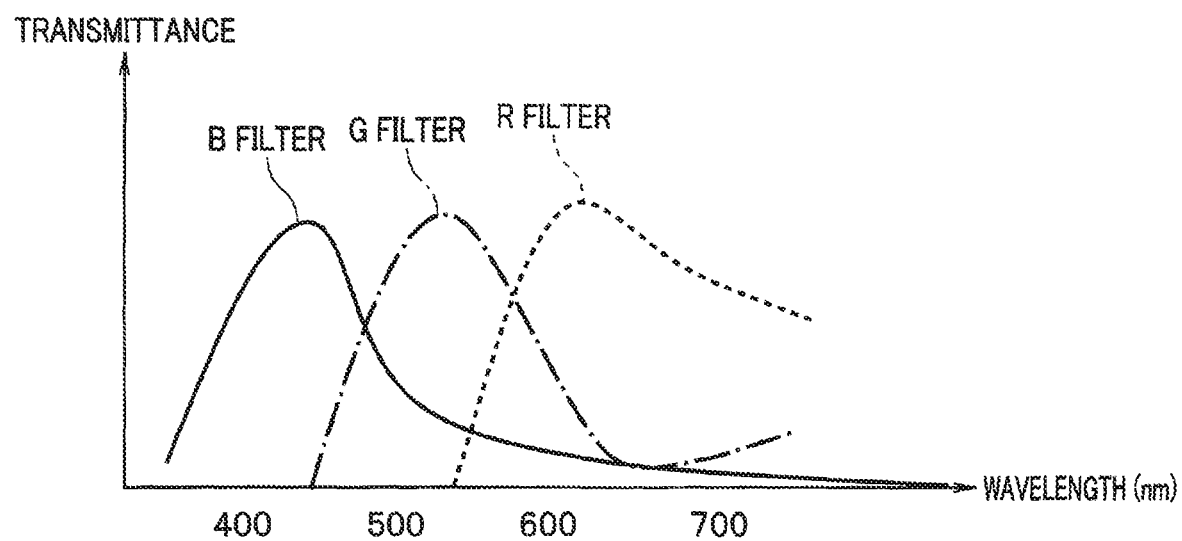
FIG. 2 is a view illustrating an example of transmission characteristics of a primary color filter used in the biological observation system according to the embodiment.
Figure 3:
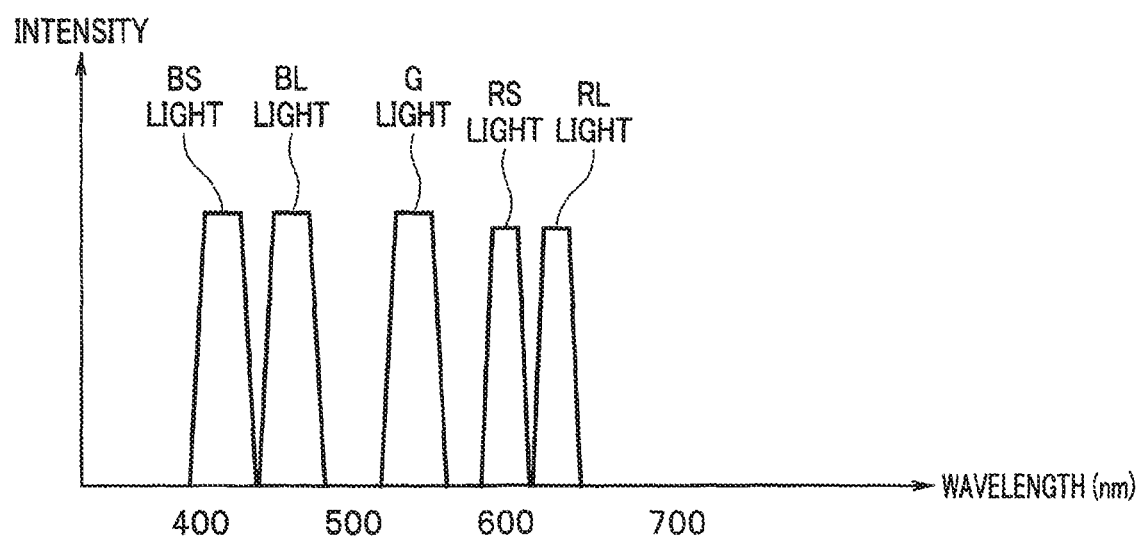
FIG. 3 is a view illustrating an example of wavelength bands of light emitted from an LED unit of the biological observation system according to the embodiment.

FIG. 1 to FIG. 3 relate to an embodiment of the present invention.

As illustrated in FIG. 1, a biological observation system 1 includes: an endoscope 2 that can be inserted into a subject and that is configured to pick up an image of an object such as living tissue inside the subject and output an image pickup signal; a light source apparatus 3 configured to supply illuminating light to be used for observation of the object through a light guide 7 inserted through and disposed inside the endoscope 2; a processor 4 configured to generate and output a video signal or the like in accordance with an image pickup signal outputted from the endoscope 2; a display apparatus 5 configured to display an observation image or the like in accordance with a video signal outputted from the processor 4; and an input apparatus 6 equipped with a switch and/or a button or the like that enables an instruction in accordance with an input operation by a user such as a surgeon to be made with respect to the processor 4. FIG. 1 is a view illustrating the configuration of main components of the biological observation system according to an embodiment of the present invention.

The endoscope 2 has an insertion portion 2a formed in an elongated shape that can be inserted into a subject, and an operation portion 2b provided on the proximal end side of the insertion portion 2a. The endoscope 2, for example, is configured to be detachably connected to the processor 4 through a universal cable (not illustrated in the drawings) having a built-in signal wire that is used for transmission of various signals such as an image pickup signal outputted from an image pickup portion 21. Further, the endoscope 2 is configured to be detachably connected to the light source apparatus 3 through a light guide cable (not illustrated in the drawings) that contains at least one part of the light guide 7.

The image pickup portion 21 for picking up an image of an object such as living tissue inside a subject, an emission end portion of the light guide 7, and an illumination optical system 22 configured to irradiate illuminating light transmitted by the light guide 7 toward an object are provided in a distal end portion 2c of the insertion portion 2a.

The image pickup portion 21 is configured to pick up an image of return light from an object that was illuminated by illuminating light emitted via the illumination optical system 22, and output an image pickup signal. Specifically, the image pickup portion 21 includes an objective optical system 21a configured to form an image of return light emitted from an object, and an image pickup device 21b in which a plurality of pixels for receiving the return light to pick up an image are disposed in a matrix in accordance with image formation positions of the objective optical system 21a and in which a primary color filter 21f is arranged in front of the plurality of pixels.

The image pickup device 21b includes, for example, an image sensor such as a CCD or a CMOS, and is configured to generate an image pickup signal by picking up an image of return light that passed through the primary color filter 21*f*, and output the image pickup signal that is generated.

The primary color filter 21*f* is formed by disposing minute color filters of the colors R (red), G (green) and B (blue) in a mosaic shape in a Bayer array at positions corresponding to the respective pixels of the image pickup device 21*b*.

The R filters, G filters and B filters of the primary color filter 21*f* are formed, for example, to have the respective transmission characteristics illustrated in FIG. 2. FIG. 2 is a view illustrating one example of the transmission characteristics of the primary color filter used in the biological observation system according to the embodiment.

As illustrated in FIG. 2, the R filter of the primary color filter 21*f* is formed so that the transmittance in a range from the red region to the near-infrared region becomes relatively higher than transmittances in the other wavelength bands.

As illustrated in FIG. 2, the G filter of the primary color filter 21*f* is formed so that the transmittance in the green region becomes relatively higher than transmittances in the other wavelength bands.

As illustrated in FIG. 2, the B filter of the primary color filter 21*f* is formed so that the transmittance in the blue region becomes relatively higher than transmittances in the other wavelength bands.

That is, in the image pickup device 21*b* of the present embodiment, a plurality of pixels are provided that have spectral sensitivities such that a sensitivity to any one color among a predetermined plurality of colors becomes relatively higher than a sensitivity to colors other than the one color. Specifically, in the image pickup device 21*b* of the present embodiment, R pixels that are pixels having a spectral sensitivity such that a sensitivity to red is relatively higher than a sensitivity to colors other than red, G pixels that are pixels having a spectral sensitivity such that a sensitivity to green is relatively higher than a sensitivity to colors other than green, and B pixels that are pixels having a spectral sensitivity such that a sensitivity to blue is relatively higher than a sensitivity to colors other than blue are provided.

The operation portion 2*b* is configured to have a shape that enables a user to grasp and operate the operation portion 2*b*. In the operation portion 2*b*, a scope switch 23 is provided that is configured to include one or more switches that can send an instruction to the processor 4 in accordance with an input operation of the user.

Further, inside the operation portion 2*b* is provided a scope memory 24 in which endoscope information including information that can identify spectral sensitivity characteristics of the image pickup device 21*b* that are defined in accordance with the spectral sensitivities of the R pixels, G pixels and B pixels and the like is stored. Note that the endoscope information stored in the scope memory 24 is read by a control portion 47 (described later) of the processor 4 when the endoscope 2 and the processor 4 are electrically connected and the power of the processor 4 is turned on.

The light source apparatus 3 is configured to include an LED drive portion 31, an LED unit 32 and a condenser lens 33.

The LED drive portion 31 is configured to include, for example, a drive circuit. The LED drive portion 31 is configured to generate and output an LED driving signal for driving respective LEDs of the LED unit 32 in accordance with an illumination control signal and a light-adjusting signal outputted from the processor 4.

The LED unit 32, for example, is configured to include LEDs 32*a* to 32*e* that are light sources that emit light of five wavelength bands that are mutually different as illustrated in FIG. 3. An optical element (not illustrated in the drawings) such as a dichroic mirror for polarizing light emitted from the LEDs 32*a* to 32*e* and making the light incident on the condenser lens 33 is also provided in the LED unit 32. FIG. 3 is a view that illustrates one example of the wavelength bands of light emitted from the LED unit of the biological observation system according to the embodiment.

The LEDs 32*a* to 32*e* are configured to individually emit light or to stop emitting light at a timing that is in accordance with an LED driving signal outputted from the LED drive portion 31. The LEDs 32*a* to 32*e* are also configured to emit light having an emission intensity in accordance with an LED driving signal outputted from the LED drive portion 31.

For example, as illustrated in FIG. 3, the LED 32*a* is configured to emit BS light that is light whose center wavelength is set to 415 nm and which is set so that the wavelength band thereof belongs to the blue region. That is, the BS light has characteristics such that the light scatters and/or reflects at capillary vessels that are present in a surface layer of living tissue, and such that an absorption coefficient for blood is higher than an absorption coefficient for blood of BL light that is described later.

For example, as illustrated in FIG. 3, the LED 32*b* is configured to emit BL light that is light whose center wavelength is set to 460 nm and which is set so that the wavelength band thereof belongs to the blue region. That is, the BL light has characteristics such that the light scatters and/or reflects at capillary vessels that are present in a surface layer of living tissue, and such that an absorption coefficient for blood is lower than the absorption coefficient for blood of the BS light.

For example, as illustrated in FIG. 3, the LED 32*c* is configured to emit G light that is light whose center wavelength is set to 540 nm and which is set so that the wavelength band thereof belongs to the green region. That is, the G light has characteristics such that the light scatters and/or reflects at blood vessels that are present in an intermediate layer that is on a surface layer side relative to a deep part of living tissue. Note that the G light may be broad-band light that includes wavelength bands other than a wavelength band in the green region.

For example, as illustrated in FIG. 3, the LED 32*d* is configured to emit RS light that is light whose center wavelength is set to 600 nm and which is set so that the wavelength band thereof belongs to the red region. That is, the RS light has characteristics such that the light scatters and/or reflects at blood vessels with a large diameter that are present in a deep part of living tissue, and such that an absorption coefficient for blood is higher than an absorption coefficient for blood of RL light that is described later.

For example, as illustrated in FIG. 3, the LED 32*e* is configured to emit RL light that is light whose center wavelength is set to 630 nm and which is set so that the wavelength band thereof belongs to the red region. That is, the RL light has characteristics such that the light scatters and/or reflects at blood vessels with a large diameter that are present in a deep part of living tissue, and such that an absorption coefficient for blood is lower than the absorption coefficient for blood of the RS light.

The condenser lens 33 is configured to converge light emitted from the LED unit 32 and make the light incident on an incident end portion of the light guide 7.

The processor 4 is configured to include a pre-processing portion 41, an A/D conversion portion 42, a color separation processing portion 43, a color balance processing portion (hereafter, abbreviated as "CB processing portion) 44, a buffer portion 45, a display control portion 46, the control portion 47 and a light-adjusting portion 48.

The pre-processing portion 41 is configured to include, for example, a signal processing circuit. The pre-processing portion 41 is configured to perform predetermined signal processing such as amplification and noise removal on an image pickup signal outputted from the image pickup portion 21 of the endoscope 2, and output the resulting image pickup signal to the A/D conversion portion 42.

The A/D conversion portion 42 is configured to include, for example, an A/D conversion circuit. Further, the A/D conversion portion 42 is configured to generate image data by performing processing such as A/D conversion on an image pickup signal outputted from the pre-processing portion 41, and output the generated image data to the color separation processing portion 43.

The color separation processing portion 43 is configured to include, for example, an arithmetic processing circuit that is capable of performing color separation processing that is described later. Further, the color separation processing portion 43 is configured to perform color separation processing for separating, from respective color components included in image data outputted from the A/D conversion portion 42, a color component obtained when an image of light of a predetermined wavelength band included in return light for which an image was picked up by the image pickup device 21b is picked up by pixels for which a sensitivity to the light of the predetermined wavelength band is greatest among the R pixels, G pixels and B pixels. The color separation processing portion 43 is also configured to perform color separation processing using a color separation matrix in accordance with control of the control portion 47. Further, the color separation processing portion 43 is configured to output monochrome image data corresponding to respective color components obtained by the color separation processing to the CB processing portion 44 and the light-adjusting portion 48.

The CB processing portion 44 is configured to include, for example, a color balance processing circuit. The CB processing portion 44 is configured to perform color balance processing on image data outputted from the color separation processing portion 43, and output the resulting image data on which the color balance processing was performed to the buffer portion 45.

The buffer portion 45 is configured to include, for example, a buffer circuit such as a buffer memory. The buffer portion 45 is configured to, in accordance with control by the control portion 47, temporarily accumulate image data outputted from the CB processing portion 44, and to output the accumulated image data to the display control portion 46.

The display control portion 46 is configured to include, for example, a display control circuit. The display control portion 46 is configured to, in accordance with control by the control portion 47, generate a video signal by allocating image data outputted from the buffer portion 45 to an R channel, a G channel, and a B channel of the display apparatus 5, and to output the generated video signal to the display apparatus 5.

The control portion 47 includes, for example, a control circuit constituted by an FPGA or a CPU or the like. The control portion 47 has a memory 47a in which Q color separation matrixes that can be utilized for color separation processing by the color separation processing portion 43 are stored in advance. Note that the aforementioned Q color separation matrixes are individually stored in the memory 47a in, for example, the form of a look-up table. Further, the number Q of color separation matrixes stored in the memory 47a is equal to or greater than a number N (2≤N) of illumination periods included in a single cycle of a time-division illumination pattern (described later).

The control portion 47 is configured to identify spectral sensitivity characteristics of the image pickup device 21b based on endoscope information read from the scope memory 24, set a time-division illumination pattern in accordance with the identified spectral sensitivity characteristics, generate an illumination control signal for illuminating an object according to the time-division illumination pattern that is set, and output the generated illumination control signal to the LED drive portion 31. Note that the aforementioned time-division illumination pattern is set, for example, as a pattern so that a combination of a plurality of wavelength bands included in illuminating light supplied from the light source apparatus 3 differs for each of N illumination periods.

The control portion 47 is configured to selectively read in from the memory 47a a color separation matrix corresponding to a combination of a plurality of wavelength bands included in return light is generated when the object is illuminated using the illumination pattern, based on the spectral sensitivity characteristics of the image pickup device 21b, and the time-division illumination pattern that was set as described above, and to also perform control with respect to the color separation processing portion 43 for causing the color separation processing portion 43 to perform color separation processing using the color separation matrix that was read in.

The control portion 47 is configured to perform control with respect to the buffer portion 45 to cause the buffer portion 45 to accumulate and output image data in accordance with the time-division illumination pattern that was set as described above.

The control portion 47 is configured to perform control with respect to the display control portion 46 for changing an observation image to be displayed on the display apparatus 5, in accordance with a desired observation mode selected from among a plurality of observation modes that can be switched by means of an observation mode switching switch (not illustrated in the drawings) that is provided at the input apparatus 6 and/or at the scope switch 23.

The light-adjusting portion 48 is configured to include, for example, a light-adjusting circuit. The light-adjusting portion 48 is configured to generate a light-adjusting signal for adjusting the light emission intensity at each LED of the LED unit 32 based on image data outputted from the color separation processing portion 43, and to output the generated light-adjusting signal to the LED drive portion 31.

Next, specific operations and the like of the biological observation system 1 according to the present embodiment will be described.

First, after connecting the respective portions of the biological observation system 1 and turning on the power, the user, for example, performs an operation to switch an illumination switch (not illustrated in the drawings) provided in the scope switch 23 and/or the input apparatus 6 from off to on to thereby issue an instruction to the control portion 47 to cause illuminating light to be supplied from the light source apparatus 3 to the endoscope 2.

When the endoscope 2 and the processor 4 are electrically connected and the power of the processor 4 is turned on, the control portion 47 reads in endoscope information stored in the scope memory 24. Further, when reading of the endoscope information from the scope memory 24 is completed, the control portion 47 identifies spectral sensitivity characteristics of the image pickup device 21b based on the endoscope information, and sets a time-division illumination pattern that is in accordance with the identified spectral sensitivity characteristics.

Specifically, for example, in a case where, based on the endoscope information read in from the scope memory 24, the control portion 47 identifies that the image pickup device 21b has spectral sensitivity characteristics in accordance with the transmission characteristics of the R filter, G filter and B filter illustrated in FIG. 2, as a time-division illumination pattern that is in accordance with the identified spectral sensitivity characteristics, the control portion 47 sets an illumination pattern IP1 in which an illumination period PA that causes the LEDs 32a, 32c and 32e to simultaneously emit light and an illumination period PB that causes the LEDs 32b and 32d to simultaneously emit light are alternately repeated. That is, the illumination pattern IP1 is set as an illumination pattern which adopts the two illumination periods PA and PB as an illumination period PAB for a single cycle.

Upon detecting that an instruction has been made for causing illuminating light to be supplied from the light source apparatus 3 to the endoscope 2, the control portion 47 generates an illumination control signal for illuminating an object using the illumination pattern IP1, and outputs the illumination control signal to the LED drive portion 31.

In response to the illumination control signal outputted from the control portion 47, the LED drive portion 31 generates an LED driving signal for causing the LEDs 32a, 32c and 32e to simultaneously emit light while stopping the LEDs 32b and 32d from emitting light in the illumination period PA, and for causing the LEDs 32b and 32d to simultaneously emit light while stopping the LEDs 32a, 32c and 32e from emitting light in the illumination period PB, and outputs the generated LED driving signal to the LED unit 32.

That is, according to the illumination pattern IP1 described above, in the illumination period PA, illuminating light including the three wavelength bands of BS light, G light and RL light is supplied from the light source apparatus 3, return light (reflected light) LA including the three wavelength bands in question is emitted from the object which was illuminated by the illuminating light, and an image of the return light LA that passed through the primary color filter 21f is picked up by the image pickup device 21b. Further, according to the illumination pattern IP1 described above, in the illumination period PB, illuminating light including the two wavelength bands of BL light and RS light is supplied from the light source apparatus 3, return light (reflected light) LB including the two wavelength bands in question is emitted from the object that was illuminated by the illuminating light, and an image of the return light LB that passed through the primary color filter 21f is picked up by the image pickup device 21b.

Based on the spectral sensitivity characteristics of the image pickup device 21b, and the illumination pattern IP1, the control portion 47 selectively reads in from the memory 47a color separation matrixes corresponding to a combination of the plurality of wavelength bands included in each of the return lights LA and LB that are generated when the object is illuminated using the illumination pattern IP1.

Specifically, in a case where the control portion 47 set the illumination pattern IP1, for example, the control portion 47 reads in from the memory 47a a color separation matrix MA for separating each of a color component CBS that is a blue color component obtained by picking up an image of BS light included in the return light LA at the B pixels, a color component CG that is a green color component obtained by picking up an image of G light included in the return light LA at the G pixels, and a color component CRL that is a red color component obtained by picking up an image of RL light included in the return light LA at the R pixels from the respective color components included in image data outputted from the A/D conversion portion 42. Further, in a case where the control portion 47 set the illumination pattern IP1, for example, the control portion 47 reads in from the memory 47a a color separation matrix MB for separating each of a color component CBL that is a blue color component obtained by picking up an image of BL light included in the return light LB at the B pixels, and a color component CRS that is a red color component obtained by picking up an image of RS light included in the return light LB at the R pixels from the respective color components included in image data outputted from the A/D conversion portion 42.

The control portion 47 performs control of the color separation processing portion 43 to cause color separation processing using the color separation matrix MA to be performed in the illumination period PA of the illumination pattern IP1 and to cause color separation processing using the color separation matrix MB to be performed in the illumination period PB of the illumination pattern IP1.

In response to the control by the control portion 47, the color separation processing portion 43 acquires the respective color components CBS, CG and CRL by performing color separation processing using the color separation matrix MA on image data outputted from the A/D conversion portion 42 during the illumination period PA, and outputs monochrome image data corresponding to the acquired color components CBS, CG and CRL to the CB processing portion 44 and the light-adjusting portion 48. Further, in response to the control by the control portion 47, the color separation processing portion 43 acquires the respective color components CBL and CRS by performing color separation processing using the color separation matrix MB on image data outputted from the A/D conversion portion 42 during the illumination period PB, and outputs monochrome image data corresponding to the acquired color components CBL and CRS to the CB processing portion 44 and the light-adjusting portion 48.

In this case, in the present embodiment, because the primary color filter 21f has the transmission characteristics illustrated in FIG. 2, an image of the BS light included in the return light LA is picked up by the B pixels of the image pickup device 21b, an image of the G light included in the return light LA is picked up by each of the B pixels, the G pixels and the R pixels of the image pickup device 21b, and an image of the RL light included in the return light LA is picked up by each of the B pixels, the G pixels and the R pixels of the image pickup device 21b. Further, in the present embodiment, because the primary color filter 21f has the transmission characteristics illustrated in FIG. 2, an image of the BL light included in the return light LB is picked up by each of the B pixels and the G pixels of the image pickup device 21b, and an image of the RS light included in the return light LB is picked up by each of the B pixels, the G pixels and the R pixels of the image pickup device 21b.

Thus, in the present embodiment, a configuration is adopted so that, by alternately switching the two color separation matrixes MA and MB to be used in the color separation processing of the color separation processing portion 43 for each illumination period of the illumination pattern IP1, appropriate color separation is performed in accordance with the combination of the plurality of wavelength bands included in the return light LA and the combination of the plurality of wavelength bands included in the return light LB.

The CB processing portion 44 is configured to perform color balance processing that multiplies luminance values of image data outputted from the color separation processing portion 43 by predetermined color balance coefficients, and outputs image data on which has undergone the color balance processing to the buffer portion 45. Note that the aforementioned color balance coefficients are, for example, set in advance as coefficients that adopt as a reference value a luminance value of image data of the color component CRS in respective pieces of image data outputted from the color separation processing portion 43 when an image of a white object that was illuminated using the illumination pattern IP1 is picked up, and uniformly align luminance values of image data of the respective color components other than the color component CRS with the reference value.

The light-adjusting portion 48 generates a light-adjusting signal for changing (increasing or decreasing) the light emission intensities of the respective LEDs of the LED unit 32 so that, for example, the luminance value of the image data of the color component CRS outputted from the color separation processing portion 43 reaches a predetermined brightness target value, and outputs the generated light-adjusting signal to the LED drive portion 31.

The control portion 47 performs control with respect to the buffer portion 45 to cause the buffer portion 45 to accumulate and output image data in accordance with the illumination pattern IP1.

In response to the control by the control portion 47, the buffer portion 45 accumulates image data of respective color components outputted from the CB processing portion 44 until an illumination period PAB for a single cycle that is obtained by adding the illumination periods PA and PB elapses, and outputs the accumulated image data for the respective color components to the display control portion 46 when the illumination period PAB for the single cycle elapses. That is, according to the above described operations of the buffer portion 45, image data of the color component CBS for a single field, image data of the color component CBL for a single field, image data of the color component CG for a single field, image data of the color component CRS for a single field and image data of the color component CRL for a single field that are respective pieces of image data acquired in accordance with the return lights LA and LB are simultaneously outputted to the display control portion 46.

The control portion 47 performs control of the display control portion 46 to change an observation image to be displayed on the display apparatus 5, in accordance with a desired observation mode selected from among a plurality of observation modes that are switchable by means of an observation mode switching switch provided at the input apparatus 6 and/or at the scope switch 23.

In response to the control by the control portion 47, for example, in a case where a normal observation mode that displays an observation image which has similar color tones as the color tones when living tissue is seen with the naked eye is selected, the display control portion 46 generates a video signal for displaying the observation image in amounts for a single frame by performing operations to allocate image data obtained by adding together image data of the color components CBS and CBL in amounts for a single field to the B channel of the display apparatus 5, allocate image data of the color component CG for a single field to the G channel of the display apparatus 5, and allocate image data obtained by adding together image data of the color components CRS and CRL in amounts for a single field to the R channel of the display apparatus 5, and outputs the generated video signal to the display apparatus 5.

Further, in response to the control by the control portion 47, for example, in a case where a narrow-band light observation mode that displays an observation image that emphasizes capillary vessels that are present in a surface layer of living tissue is selected, the display control portion 46 generates a video signal for displaying the observation image in amounts for a single frame by performing operations to allocate image data of the color component CBS for a single field to the B channel and G channel of the display apparatus 5 and allocate image data of the color component CG for a single field to the R channel of the display apparatus 5, and outputs the generated video signal to the display apparatus 5.

Further, in response to the control by the control portion 47, for example, in a case where a deep-part blood vessel observation mode that displays an observation image that emphasizes blood vessels with a large diameter that are present in a deep part of living tissue is selected, the display control portion 46 generates a video signal for displaying the observation image in amounts for a single frame by performing operations to allocate image data of the color component CG for a single field to the B channel of the display apparatus 5, allocate image data of the color component CRS for a single field to the G channel of the display apparatus 5, and allocate image data of the color component CRL for a single field to the R channel of the display apparatus 5, and outputs the generated video signal to the display apparatus 5.

Note that the present embodiment is not limited to a configuration in which operations are performed for displaying only one kind of observation image that corresponds to one observation mode among the normal observation mode, the narrow-band light observation mode and the deep-part blood vessel observation mode on the display apparatus 5, and for example a configuration may be adopted so that operations are performed for collectively displaying two or more kinds of observation images that correspond to two or more observation modes among the respective observation modes on the display apparatus 5.

As described above, according to the present embodiment, color separation processing using the color separation matrix MA is performed during the illumination period PA in which the return light LA in accordance with the illumination pattern IP1 is emitted from the object, and color separation processing using the color separation matrix MB is performed during the illumination period PB in which the return light LB in accordance with the illumination pattern IP1 is emitted from the object. Therefore, according to the present embodiment, since appropriate color separation that is in accordance with periodic changes in a combination of a plurality of wavelength bands included in return light emitted from the object can be performed, the image quality of an observation image displayed on the display apparatus 5 in a desired observation mode selected from among a plurality of observation modes such as a normal observation mode, a narrow-band light observation mode and a deep-part blood vessel observation mode can be improved.

On the other hand, according to the present embodiment, a configuration may also be adopted so that, for example, in a case where the deep-part blood vessel observation mode is selected, control is performed for illuminating the object using an illumination pattern IP2 that is different to the illumination pattern IP1, and a color separation matrix corresponding to a combination of a plurality of wavelength bands included in return light that is generated when the object is illuminated using the illumination pattern IP2 is read out from the memory 47a. Specific operations and the like of the biological observation system 1 according to this first modification will be described hereunder. Note that, in the following description, for brevity, a specific description relating to portions to which operations and the like described previously can be applied is omitted as appropriate.

Based on endoscope information read in from the scope memory 24, the control portion 47 sets an illumination pattern IP1, and a time-division illumination pattern IP2 that is different to the illumination pattern IP1.

Specifically, the control portion 47, for example, sets the illumination pattern IP2 in which an illumination period PC that causes the LEDs 32b and 32d to simultaneously emit light and an illumination period PD that causes the LEDs 32b and 32e to simultaneously emit light are alternately repeated. That is, the illumination pattern IP2 is set as an illumination pattern which adopts the two illumination periods PC and PD as an illumination period PCD for a single cycle.

Further, when an instruction for causing illuminating light to be supplied from the light source apparatus 3 to the endoscope 2 is made and the control portion 47 detects that either one of the normal observation mode and the narrow-band light observation mode is selected, the control portion 47 generates an illumination control signal for illuminating the object using the illumination pattern IP1, and outputs the generated illumination control signal to the LED drive portion 31. Furthermore, when an instruction for causing illuminating light to be supplied from the light source apparatus 3 to the endoscope 2 is made and the control portion 47 detects that the deep-part blood vessel observation mode is selected, the control portion 47 generates an illumination control signal for illuminating the object using the illumination pattern IP2, and outputs the generated illumination control signal to the LED drive portion 31.

Upon detecting that the object is to be illuminated using the illumination pattern IP1 in accordance with the illumination control signal outputted from the control portion 47, the LED drive portion 31 generates an LED driving signal for causing the respective LEDs of the LED unit 32 to emit light or not emit light as described above, and outputs the generated LED driving signal to the LED unit 32. Further, upon detecting that the object is to be illuminated using the illumination pattern IP2 in accordance with the illumination control signal outputted from the control portion 47, the LED drive portion 31 generates an LED driving signal for causing the LEDs 32b and 32d to simultaneously emit light while causing the LEDs 32a, 32c and 32e not to emit light in the illumination period PC, and for causing the LEDs 32b and 32e to simultaneously emit light while causing the LEDs 32a, 32c and 32d not to emit light in the illumination period PD, and outputs the generated LED driving signal to the LED unit 32.

That is, according to the illumination pattern IP2 described above, the LED 32b continues to emit light constantly during the illumination periods PC and PD. Further, according to the illumination pattern IP2 as described above, in the illumination period PC, illuminating light including the two wavelength bands of BL and RS light is supplied from the light source apparatus 3, return light (reflected light) LC including the two wavelength bands in question is emitted from the object that was illuminated by the illuminating light, and an image of the return light LC that passed through the primary color filter 21f is picked up by the image pickup device 21b. Further, according to the illumination pattern IP2 described above, in the illumination period PD, illuminating light including the two wavelength bands of BL light and RL light is supplied from the light source apparatus 3, return light (reflected light) LD including the two wavelength bands in question is emitted from the object that was illuminated by the illuminating light, and an image of the return light LD that passed through the primary color filter 21f is picked up by the image pickup device 21b.

Based on the spectral sensitivity characteristics of the image pickup device 21b, and the illumination pattern IP1, the control portion 47 selectively reads in from the memory 47a color separation matrixes corresponding to a combination of the plurality of wavelength bands included in each of the return lights LA and LB that are generated when the object is illuminated using the illumination pattern IP1. Further, based on the spectral sensitivity characteristics of the image pickup device 21b, and the illumination pattern IP2, the control portion 47 selectively reads in from the memory 47a color separation matrixes corresponding to a combination of the plurality of wavelength bands included in each of the return lights LC and LD that are generated when the object is illuminated using the illumination pattern IP2.

Specifically, in a case where the control portion 47 set the illumination pattern IP1, the aforementioned color separation matrixes MA and MB are each read in from the memory 47a. Further, in a case where the control portion 47 set the illumination pattern IP2, for example, the control portion 47 reads in from the memory 47a a color separation matrix MC for separating each of a color component CBL that is a blue color component obtained by picking up an image of BL light included in the return light LC at the B pixels, and a color component CRS that is a red color component obtained by picking up an image of RS light included in the return light LC at the R pixels from the respective color components included in image data outputted from the A/D conversion portion 42. Furthermore, in a case where the control portion 47 set the illumination pattern IP2, for example, the control portion 47 reads in from the memory 47a a color separation matrix MD for separating each of a color component CBL that is a blue color component obtained by picking up an image of BL light included in the return light LD at the B pixels, and a color component CRL that is a red color component obtained by picking up an image of RL light included in the return light LD at the R pixels from the respective color components included in image data outputted from the A/D conversion portion 42.

Upon detecting that either one of the normal observation mode and the narrow-band light observation mode is selected, the control portion 47 performs control of the color separation processing portion 43 to cause color separation processing using the color separation matrix MA to be performed in the illumination period PA of the illumination pattern IP1 and to cause color separation processing using the color separation matrix MB to be performed in the illumination period PB of the illumination pattern IP1. Further, upon detecting that the deep-part blood vessel observation mode is selected, the control portion 47 performs control of the color separation processing portion 43 to cause color separation processing using the color separation matrix MC to be performed in the illumination period PC of the illumination pattern IP2 and to cause color separation processing using the color separation matrix MD to be performed in the illumination period PD of the illumination pattern IP2.

In response to the control by the control portion 47, the color separation processing portion 43 acquires the respective color components CBL and CRS by performing color separation processing using the color separation matrix MC on image data outputted from the A/D conversion portion 42 during the illumination period PC, and outputs monochrome image data corresponding to the acquired color components CBL and CRS to the CB processing portion 44 and the light-adjusting portion 48. Further, in response to the control by the control portion 47, the color separation processing portion 43 acquires the respective color components CBL and CRL by performing color separation processing using the color separation matrix MD on image data outputted from the A/D conversion portion 42 during the illumination period PD, and outputs monochrome image data corresponding to the acquired color components CBL and CRL to the CB processing portion 44 and the light-adjusting portion 48.

In this case, in the present modification, because the primary color filter 21f has the transmission characteristics illustrated in FIG. 2, an image of the BL light included in the return light LC is picked up by each of the B pixels and the G pixels of the image pickup device 21b, and an image of the RS light included in the return light LC is picked up by each of the B pixels, the G pixels and the R pixels of the image pickup device 21b. Further, in the present modification, because the primary color filter 21f has the transmission characteristics illustrated in FIG. 2, an image of the BL light included in the return light LD is picked up by each of the B pixels and the G pixels of the image pickup device 21b, and an image of the RL light included in the return light LD is picked up by each of the B pixels, the G pixels and the R pixels of the image pickup device 21b.

Thus, in the present modification, a configuration is adopted so that, when the deep-part blood vessel observation mode is selected, by alternately switching the two color separation matrixes MC and MD to be used in the color separation processing of the color separation processing portion 43 for each illumination period of the illumination pattern IP2, appropriate color separation is performed in accordance with the combination of the plurality of wavelength bands included in the return light LC and the combination of the plurality of wavelength bands included in the return light LD.

Upon detecting that either one of the normal observation mode and the narrow-band light observation mode is selected, the control portion 47 performs control with respect to the buffer portion 45 to cause the buffer portion 45 to accumulate and output image data in accordance with the illumination pattern IP1. Further, upon detecting that the deep-part blood vessel observation mode is selected, the control portion 47 performs control with respect to the buffer portion 45 to cause the buffer portion 45 to accumulate and output image data in accordance with the illumination pattern IP2.

When either one of the normal observation mode and the narrow-band light observation mode is selected, in response to the control by the control portion 47, the buffer portion 45 accumulates image data of each color component outputted from the CB processing portion 44 until an illumination period PAB for a single cycle that is obtained by adding the illumination periods PA and PB elapses, and outputs the accumulated image data for the respective color components to the display control portion 46 when the illumination period PAB for the single cycle elapses. Further, when the deep-part blood vessel observation mode is selected, in response to the control by the control portion 47, the buffer portion 45 accumulates image data of each color component outputted from the CB processing portion 44 until an illumination period PCD for a single cycle that is obtained by adding the illumination periods PC and PD elapses, and outputs the accumulated image data for the respective color components to the display control portion 46 when the illumination period PCD for the single cycle elapses. That is, according to the above described operations of the buffer portion 45, in a case where either one of the normal observation mode and the narrow-band light observation mode is selected, image data of the color component CBS for a single field, image data of the color component CBL for a single field, image data of the color component CG for a single field, image data of the color component CRS for a single field and image data of the color component CRL for a single field that are respective pieces of image data acquired in accordance with the return lights LA and LB are simultaneously outputted to the display control portion 46. Further, according to the above described operations of the buffer portion 45, in a case where the deep-part blood vessel observation mode is selected, image data of the color component CBL for two fields, image data of the color component CRS for a single field and image data of the color component CRL for a single field that are respective pieces of image data obtained in accordance with the return lights LC and LD are simultaneously outputted to the display control portion 46.

In a case where the deep-part blood vessel observation mode is selected, in response to the control by the control portion 47, the display control portion 46 generates a video signal for displaying an observation image for the deep-part blood vessel observation mode in amounts for a single frame by performing operations to allocate image data obtained by adding together the image data of the color component CBL for two fields to the B channel of the display apparatus 5, allocate image data of the color component CRS for a single field to the G channel of the display apparatus 5, and allocate image data of the color component CRL for a single field to the R channel of the display apparatus 5, and outputs the generated video signal to the display apparatus 5. According to such operations of the display control portion 46, for example, in comparison to a case where image data of the color component CBL for a single field is allocated to the B channel of the display apparatus 5, the signal-to-noise ratio for the B channel of the observation image to be displayed on the display apparatus 5 can be improved.

Note that, in the present modification, in a case where the deep-part blood vessel observation mode is selected, for example, a configuration may be adopted so as to allocate image data for a single field that is obtained as an average of image data of the color component CBL for two fields to the B channel of the display apparatus 5, or a configuration may be adopted so as to allocate image data of the color component CBL for a single field obtained in accordance with the return light LC (obtained by color separation processing using the color separation matrix MC) to the B channel of the display apparatus 5.

Further, for example, in a case where an observation mode KMA that is a different observation mode to each of the normal observation mode, the narrow-band light observation mode and the deep-part blood vessel observation mode is selected, the display control portion 46 of the present modification may be configured to generate a video signal for displaying an observation image for the observation mode KMA in amounts for a single frame by performing signal processing for emphasizing blood vessels with respect to the image data of the color components CRS and CRL and also performing operations to allocate image data to each of the B channel and G channel of the display apparatus 5 using at least one piece of image data among pieces of image data of the color component CBL for two fields, and allocate image data to the R channel of the display apparatus 5 using the image data of the color components CRS and CRL on which the signal processing was performed. Note that, in the case of performing the foregoing operations, the image data to be allocated to the B channel and the G channel, respectively, of the display apparatus 5 may be any one piece of image data among the pieces of image data of the color component CBL for two fields or may be image data obtained by addition or averaging of the pieces of image data of the color component CBL for two fields. Further, in the case of performing the foregoing operations, the image data to be allocated to the R channel of the display apparatus 5 may be any one piece of image data among the pieces of image data of the color components CRS and CRL on which the aforementioned signal processing was performed or may be image data obtained by addition or averaging of the pieces of image data of the color components CRS and CRL on which the aforementioned signal processing was performed.

As described above, according to the present modification, in a case where the deep-part blood vessel observation mode is selected, color separation processing using the color separation matrix MC is performed during the illumination period PC in which the return light LC that is in accordance with the illumination pattern IP2 is emitted from the object, and color separation processing using the color separation matrix MD is performed during the illumination period PD in which the return light LD that is in accordance with the illumination pattern IP2 is emitted from the object. Therefore, according to the present modification, in the deep-part blood vessel observation mode, since appropriate color separation that is in accordance with periodic changes in a combination of a plurality of wavelength bands included in return light that is emitted from the object can be performed, the image quality of an observation image displayed on the display apparatus 5 can be improved.

On the other hand, according to the present embodiment, a configuration may also be adopted so that, for example, in a case where the deep-part blood vessel observation mode is selected, control is performed for illuminating the object using an illumination pattern IP3 that is different to each of the illumination patterns IP1 and IP2, and color separation matrixes corresponding to combinations of a plurality of wavelength bands included in return light generated when the object is illuminated using the illumination pattern IP3 are read out from the memory 47a. Specific operations and the like of the biological observation system 1 according to this second modification will be described hereunder.

Based on endoscope information that was read in from the scope memory 24, the control portion 47 sets an illumination pattern IP1 and a time-division illumination pattern IP3 that is different to the illumination pattern IP1.

Specifically, the control portion 47, for example, sets the illumination pattern IP3 in which an illumination period PE that causes the LEDs 32c and 32d to simultaneously emit light and an illumination period PF that causes the LEDs 32c and 32e to simultaneously emit light are alternately repeated. That is, the illumination pattern IP3 is set as an illumination pattern which adopts the two illumination periods PE and PF as an illumination period PEF for a single cycle.

Further, when an instruction for causing illuminating light to be supplied from the light source apparatus 3 to the endoscope 2 is made and the control portion 47 detects that either one of the normal observation mode and the narrow-band light observation mode is selected, the control portion 47 generates an illumination control signal for illuminating the object using the illumination pattern IP1, and outputs the generated illumination control signal to the LED drive portion 31. Furthermore, when an instruction for causing illuminating light to be supplied from the light source apparatus 3 to the endoscope 2 is made and the control portion 47 detects that the deep-part blood vessel observation mode is selected, the control portion 47 generates an illumination control signal for illuminating the object using the illumination pattern IP3, and outputs the generated illumination control signal to the LED drive portion 31.

Upon detecting that the object is to be illuminated using the illumination pattern IP1 in response to the illumination control signal outputted from the control portion 47, the LED drive portion 31 generates an LED driving signal for causing the respective LEDs of the LED unit 32 to emit light or not emit as described above, and outputs the generated LED driving signal to the LED unit 32. Further, upon detecting that the object is to be illuminated using the illumination pattern IP3 in response to the illumination control signal outputted from the control portion 47, the LED drive portion 31 generates an LED driving signal for causing the LEDs 32c and 32d to simultaneously emit light while causing the LEDs 32a, 32b and 32e to not emit light in the illumination period PE, and for causing the LEDs 32c and 32e to simultaneously emit light while causing the LEDs 32a, 32b and 32d to not emit light in the illumination period PF, and outputs the generated LED driving signal to the LED unit 32.

That is, according to the illumination pattern IP3 described above, the LED 32c continues to emit light constantly during the illumination periods PE and PF. Further, according to the illumination pattern IP3 described above, in the illumination period PE, illuminating light including the two wavelength bands of G and RS light is supplied from the light source apparatus 3, return light (reflected light) LE including the two wavelength bands in question is emitted from the object that was illuminated by the illuminating light, and an image of the return light LE that passed through the primary color filter 21f is picked up by the image pickup device 21b. Further, according to the illumination pattern IP3 described above, in the illumination period PF, illuminating light including the two wavelength bands of G light and RL light is supplied from the light source apparatus 3, return light (reflected light) LF including the two wavelength bands in question is emitted from the object that was illuminated by the illuminating light, and an image of the return light LF that passed through the primary color filter 21f is picked up by the image pickup device 21b.

Based on the spectral sensitivity characteristics of the image pickup device 21b, and the illumination pattern IP1, the control portion 47 selectively reads in from the memory 47a color separation matrixes corresponding to a combination of the plurality of wavelength bands included in each of the return lights LA and LB that are generated when the object is illuminated using the illumination pattern IP1. Further, based on the spectral sensitivity characteristics of the image pickup device 21b, and the illumination pattern IP3, the control portion 47 selectively reads in from the memory 47a color separation matrixes corresponding to a combination of the plurality of wavelength bands included in each of the return lights LE and LF that are generated when the object is illuminated using the illumination pattern IP3.

Specifically, in a case where the control portion 47 sets the illumination pattern IP1, the aforementioned color separation matrixes MA and MB are each read in from the memory 47a. Further, in a case where the control portion 47 sets the illumination pattern IP3, for example, the control portion 47 reads in from the memory 47a a color separation matrix ME for separating each of a color component CG that is a green color component obtained by picking up an image of G light included in the return light LE at the G pixels, and a color component CRS that is a red color component obtained by picking up an image of RS light included in the return light LE at the R pixels from the respective color components included in image data outputted from the A/D conversion portion 42. Furthermore, in a case where the control portion 47 sets the illumination pattern IP3, for example, the control portion 47 reads in from the memory 47a a color separation matrix MF for separating each of a color component CG that is a green color component obtained by picking up an image of G light included in the return light LF at the G pixels, and a color component CRL that is a red color component obtained by picking up an image of RL light included in the return light LF at the R pixels from the respective color components included in image data outputted from the A/D conversion portion 42.

Upon detecting that either one of the normal observation mode and the narrow-band light observation mode is selected, the control portion 47 performs control of the color separation processing portion 43 to cause color separation processing using the color separation matrix MA to be performed in the illumination period PA of the illumination pattern IP1 and to cause color separation processing using the color separation matrix MB to be performed in the illumination period PB of the illumination pattern IP1. Further, upon detecting that the deep-part blood vessel observation mode is selected, the control portion 47 performs control of the color separation processing portion 43 to cause color separation processing using the color separation matrix ME to be performed in the illumination period PE of the illumination pattern IP3 and to cause color separation processing using the color separation matrix MF to be performed in the illumination period PF of the illumination pattern IP3.

In response to the control by the control portion 47, the color separation processing portion 43 acquires the respective color components CG and CRS by performing color separation processing using the color separation matrix ME on image data outputted from the A/D conversion portion 42 during the illumination period PE, and outputs monochrome image data corresponding to the acquired color components CG and CRS to the CB processing portion 44 and the light-adjusting portion 48. Further, in response to the control by the control portion 47, the color separation processing portion 43 acquires the respective color components CG and CRL by performing color separation processing using the color separation matrix MF on image data outputted from the A/D conversion portion 42 during the illumination period PF, and outputs monochrome image data corresponding to the acquired color components CG and CRL to the CB processing portion 44 and the light-adjusting portion 48.

In this case, in the present modification, because the primary color filter 21f has the transmission characteristics illustrated in FIG. 2, an image of G light included in the return light LE is picked up by each of the B pixels, the G pixels and the R pixels of the image pickup device 21b, and an image of the RS light included in the return light LE is picked up by each of the B pixels, the G pixels and the R pixels of the image pickup device 21b. Further, in the present modification, because the primary color filter 21f has the transmission characteristics illustrated in FIG. 2, an image of the G light included in the return light LF is picked up by each of the B pixels, the G pixels and the R pixels of the image pickup device 21b, and an image of the RL light included in the return light LF is picked up by each of the B pixels, the G pixels and the R pixels of the image pickup device 21b.

Thus, in the present modification, a configuration is adopted so that, when the deep-part blood vessel observation mode is selected, by alternately switching the two color separation matrixes ME and MF to be used in the color separation processing of the color separation processing portion 43 for each illumination period of the illumination pattern IP3, appropriate color separation is performed in accordance with the combination of the plurality of wavelength bands included in the return light LE and the combination of the plurality of wavelength bands included in the return light LF.

Upon detecting that either one of the normal observation mode and the narrow-band light observation mode is selected, the control portion 47 performs control with respect to the buffer portion 45 to cause the buffer portion 45 to accumulate and output image data in accordance with the illumination pattern IP1. Further, upon detecting that the deep-part blood vessel observation mode is selected, the control portion 47 performs control with respect to the buffer portion 45 to cause the buffer portion 45 to accumulate and output image data in accordance with the illumination pattern IP3.

When either one of the normal observation mode and the narrow-band light observation mode is selected, in response to the control by the control portion 47, the buffer portion 45 accumulates image data of each color component outputted from the CB processing portion 44 until an illumination period PAB for a single cycle that is obtained by adding the illumination periods PA and PB elapses, and outputs the accumulated image data for the respective color components to the display control portion 46 when the illumination period PAB for the single cycle elapses. Further, when the deep-part blood vessel observation mode is selected, in response to the control by the control portion 47, the buffer portion 45 accumulates image data of each color component outputted from the CB processing portion 44 until an illumination period PEF for a single cycle that is obtained by adding the illumination periods PE and PF elapses, and outputs the accumulated image data for the respective color components to the display control portion 46 when the illumination period PEF for the single cycle elapses. That is, according to the above described operations of the buffer portion 45, in a case where the deep-part blood vessel observation mode is selected, image data of the color component CG for two fields, image data of the color component CRS for a single field and image data of the color component CRL for a single field that are respective pieces of image data obtained in accordance with the return lights LE and LF are simultaneously outputted to the display control portion 46.

In a case where the deep-part blood vessel observation mode is selected, in response to the control by the control portion 47, the display control portion 46 generates a video signal for displaying an observation image for the deep-part blood vessel observation mode in amounts for a single frame by performing operations to allocate image data obtained by adding together the image data of the color component CG for two fields to the B channel of the display apparatus 5, allocate image data of the color component CRS for a single field to the G channel of the display apparatus 5, and allocate image data of the color component CRL for a single field to the R channel of the display apparatus 5, and outputs the generated video signal to the display apparatus 5. According to such operations of the display control portion 46, for example, in comparison to a case where image data of the color component CG for a single field is allocated to the B channel of the display apparatus 5, the signal-to-noise ratio for the B channel of the observation image to be displayed on the display apparatus 5 can be improved.

Note that, in the present modification, in a case where the deep-part blood vessel observation mode is selected, for example, a configuration may be adopted so as to allocate image data corresponding to the average of image data of the color component CG for two fields to the B channel of the display apparatus 5, or a configuration may be adopted so as to allocate image data of the color component CG for a single field obtained in accordance with the return light LE (obtained by color separation processing using the color separation matrix ME) to the B channel of the display apparatus 5.

Further, for example, in a case where the deep-part blood vessel observation mode is selected, the display control portion 46 of the present modification may be configured to generate a video signal for displaying an observation image for the deep-part blood vessel observation mode in amounts for a single frame by performing signal processing for emphasizing blood vessels with respect to the image data of the color components CRS and CRL and also performing operations to allocate image data to each of the B channel and G channel of the display apparatus 5 using at least one piece of image data among pieces of image data of the color component CG for two fields, and to allocate image data to the R channel of the display apparatus 5 using the image data of the color components CRS and CRL on which the signal processing was performed. Note that, in the case of performing the foregoing operations, the image data to be allocated to the B channel and the G channel, respectively, of the display apparatus 5 may be any one piece of image data among the pieces of image data of the color component CG for two fields or may be image data obtained by addition or averaging of the pieces of image data of the color component CG for two fields. Further, in the case of performing the foregoing operations, the image data to be allocated to the R channel of the display apparatus 5 may be any one piece of image data among the pieces of image data of the color components CRS and CRL on which the aforementioned signal processing was performed or may be image data obtained by addition or averaging of the pieces of image data of the color components CRS and CRL on which the aforementioned signal processing was performed.

As described above, according to the present modification, in a case where the deep-part blood vessel observation mode is selected, color separation processing using the color separation matrix ME is performed during the illumination period PE in which the return light LE that is in accordance with the illumination pattern IP3 is emitted from the object, and color separation processing using the color separation matrix MF is performed during the illumination period PF in which the return light LF that is in accordance with the illumination pattern IP3 is emitted from the object. Therefore, according to the present modification, in the deep-part blood vessel observation mode, since appropriate color separation that is in accordance with periodic changes in a combination of a plurality of wavelength bands included in return light emitted from the object can be performed, the image quality of an observation image that is displayed on the display apparatus 5 can be improved.

On the other hand, according to the present embodiment, a configuration may also be adopted so that, for example, in a case where the deep-part blood vessel observation mode is selected, control is performed for illuminating the object using an illumination pattern IP4 that is different to each of the illumination patterns IP1 to IP3, and color separation matrixes corresponding to combinations of a plurality of wavelength bands included in return light generated when the object is illuminated using the illumination pattern IP4 are read out from the memory 47a, and an observation image in accordance with a diagnosis and treatment scene is thus displayed on the display apparatus 5. Specific operations and the like of the biological observation system 1 according to this third modification are described hereunder.

Based on endoscope information read in from the scope memory 24, the control portion 47 sets an illumination pattern IP1 and a time-division illumination pattern IP4 that is different to the illumination pattern IP1.

Specifically, the control portion 47, for example, sets the illumination pattern IP4 in which an illumination period PG that causes the LEDs 32b and 32d to simultaneously emit light and an illumination period PH that causes the LEDs 32c and 32e to simultaneously emit light are alternately repeated. That is, the illumination pattern IP4 is set as an illumination pattern which adopts the two illumination periods PG and PH as an illumination period PGH for a single cycle.

Further, when an instruction for causing illuminating light to be supplied from the light source apparatus 3 to the endoscope 2 is made and the control portion 47 detects that either one of the normal observation mode and the narrow-band light observation mode is selected, the control portion 47 generates an illumination control signal for illuminating the object using the illumination pattern IP1, and outputs the generated illumination control signal to the LED drive portion 31. Furthermore, when an instruction for causing illuminating light to be supplied from the light source apparatus 3 to the endoscope 2 is made and the control portion 47 detects that the deep-part blood vessel observation mode is selected, the control portion 47 generates an illumination control signal for illuminating the object using the illumination pattern IP4, and outputs the generated illumination control signal to the LED drive portion 31.

Upon detecting that the object is to be illuminated using the illumination pattern IP1 in response to the illumination control signal outputted from the control portion 47, the LED drive portion 31 generates an LED driving signal for causing the respective LEDs of the LED unit 32 to emit light or not emit as described above, and outputs the generated LED driving signal to the LED unit 32. Further, upon detecting that the object is to be illuminated using the illumination pattern IP4 in response to the illumination control signal outputted from the control portion 47, the LED drive portion 31 generates an LED driving signal for causing the LEDs 32b and 32d to simultaneously emit light while causing the LEDs 32a, 32c and 32e not to emit light in the illumination period PG, and for causing the LEDs 32c and 32e to simultaneously emit light while causing the LEDs 32a, 32b and 32d not to emit light in the illumination period PH, and outputs the generated LED driving signal to the LED unit 32.

That is, according to the illumination pattern IP4 as described above, in the illumination period PG, illuminating light including the two wavelength bands of BL and RS light is supplied from the light source apparatus 3, return light (reflected light) LG including the two wavelength bands in question is emitted from the object that was illuminated by the illuminating light, and an image of the return light LG that passed through the primary color filter 21f is picked up by the image pickup device 21b. Further, according to the illumination pattern IP4 described above, in the illumination period PH, illuminating light including the two wavelength bands of G light and RL light is supplied from the light source apparatus 3, return light (reflected light) LH including the two wavelength bands in question is emitted from the object that was illuminated by the illuminating light, and an image of the return light LH that passed through the primary color filter 21f is picked up by the image pickup device 21b.

Based on the spectral sensitivity characteristics of the image pickup device 21b, and the illumination pattern IP1, the control portion 47 selectively reads in from the memory 47a color separation matrixes corresponding to a combination of the plurality of wavelength bands included in each of the return lights LA and LB that are generated when the object is illuminated using the illumination pattern IP1. Further, based on the spectral sensitivity characteristics of the image pickup device 21b, and the illumination pattern IP4, the control portion 47 selectively reads in from the memory 47a color separation matrixes corresponding to a combination of the plurality of wavelength bands included in each of the return lights LG and LH that are generated when the object is illuminated using the illumination pattern IP4.

Specifically, in a case where the control portion 47 sets the illumination pattern IP1, the aforementioned color separation matrixes MA and MB are each read in from the memory 47a. Further, in a case where the control portion 47 sets the illumination pattern IP4, for example, the control portion 47 reads in from the memory 47a a color separation matrix MG for separating each of a color component CBL that is a blue color component obtained by picking up an image of BL light included in the return light LG at the B pixels, and a color component CRS that is a red color component obtained by picking up an image of RS light included in the return light LG at the R pixels from the respective color components included in image data outputted from the A/D conversion portion 42. Furthermore, in a case where the control portion 47 sets the illumination pattern IP4, for example, the control portion 47 reads in from the memory 47a a color separation matrix MH for separating each of a color component CG that is a green color component obtained by picking up an image of G light included in the return light LH at the G pixels, and a color component CRL that is a red color component obtained by picking up an image of RL light included in the return light LH at the R pixels from the respective color components included in image data outputted from the A/D conversion portion 42.

Upon detecting that either one of the normal observation mode and the narrow-band light observation mode is selected, the control portion 47 performs control of the color separation processing portion 43 to cause color separation processing using the color separation matrix MA to be performed in the illumination period PA of the illumination pattern IP1 and to cause color separation processing using the color separation matrix MB to be performed in the illumination period PB of the illumination pattern IP1. Further, upon detecting that the deep-part blood vessel observation mode is selected, the control portion 47 performs control of the color separation processing portion 43 to cause color separation processing using the color separation matrix MG to be performed in the illumination period PG of the illumination pattern IP4 and to cause color separation processing using the color separation matrix MH to be performed in the illumination period PH of the illumination pattern IP4.

In response to the control by the control portion 47, the color separation processing portion 43 acquires the respective color components CBL and CRS by performing color separation processing using the color separation matrix MG on image data outputted from the A/D conversion portion 42 during the illumination period PG, and outputs monochrome image data corresponding to the acquired color components CBL and CRS to the CB processing portion 44 and the light-adjusting portion 48. Further, in response to the control by the control portion 47, the color separation processing portion 43 acquires the respective color components CG and CRL by performing color separation processing using the color separation matrix MH on image data outputted from the A/D conversion portion 42 during the illumination period PH, and outputs monochrome image data corresponding to the acquired color components CG and CRL to the CB processing portion 44 and the light-adjusting portion 48.

In this case, in the present modification, because the primary color filter 21f has the transmission characteristics illustrated in FIG. 2, an image of BL light included in the return light LG is picked up by each of the B pixels and the G pixels of the image pickup device 21b, and an image of the RS light included in the return light LG is picked up by each of the B pixels, the G pixels and the R pixels of the image pickup device 21b. Further, in the present modification, because the primary color filter 21f has the transmission characteristics illustrated in FIG. 2, an image of the G light included in the return light LH is picked up by each of the B pixels, the G pixels and the R pixels of the image pickup device 21b, and an image of the RL light included in the return light LH is picked up by each of the B pixels, the G pixels and the R pixels of the image pickup device 21b.

Thus, in the present modification, a configuration is adopted so that, when the deep-part blood vessel observation mode is selected, by alternately switching the two color separation matrixes MG and MH to be used in the color separation processing of the color separation processing portion 43 for each illumination period of the illumination pattern IP4, appropriate color separation is performed in accordance with the combination of the plurality of wavelength bands included in the return light LG and the combination of the plurality of wavelength bands included in the return light LH.

Upon detecting that either one of the normal observation mode and the narrow-band light observation mode is selected, the control portion 47 performs control with respect to the buffer portion 45 to cause the buffer portion 45 to accumulate and output image data in accordance with the illumination pattern IP1. Further, upon detecting that the deep-part blood vessel observation mode is selected, the control portion 47 performs control with respect to the buffer portion 45 to cause the buffer portion 45 to accumulate and output image data in accordance with the illumination pattern IP4.

When either one of the normal observation mode and the narrow-band light observation mode is selected, in response to the control by the control portion 47, the buffer portion 45 accumulates image data of each color component outputted from the CB processing portion 44 until an illumination period PAB for a single cycle that is obtained by adding the illumination periods PA and PB elapses, and outputs the accumulated image data for the respective color components to the display control portion 46 when the illumination period PAB for the single cycle elapses. Further, when the deep-part blood vessel observation mode is selected, in response to the control by the control portion 47, the buffer portion 45 accumulates image data of each color component outputted from the CB processing portion 44 until an illumination period PGH for a single cycle that is obtained by adding the illumination periods PG and PH elapses, and outputs the accumulated image data for the respective color components to the display control portion 46 when the illumination period PGH for the single cycle elapses. That is, according to the above described operations of the buffer portion 45, in a case where the deep-part blood vessel observation mode is selected, image data of the color component CBL for a single field, image data of the color component CG for a single field, image data of the color component CRS for a single field and image data of the color component CRL for a single field that are respective pieces of image data obtained in accordance with the return lights LG and LH are simultaneously outputted to the display control portion 46.

In a case where the deep-part blood vessel observation mode is selected, in response to an instruction that is made using a display image switching switch (not illustrated in the drawings) provided at the input apparatus 6 and/or at the scope switch 23, the control portion 47 performs control with respect to the display control portion 46 for displaying on the display apparatus 5, for example, either one of an observation image for diagnosis that is an observation image that visualizes blood vessels that are present in an intermediate layer that is on a surface layer side relative to a deep part of living tissue while emphasizing blood vessels with a large diameter that are present at a deep part of the living tissue, and an observation image for treatment that is an observation image that, while emphasizing blood vessels with a large diameter that are present at a deep part of the living tissue, at the same time also emphasizes indigo carmine and/or fat or the like that can attract attention during the course of surgical treatment using the endoscope 2.

If a selection is made to display an observation image for diagnosis in the deep-part blood vessel observation mode, in response to the control by the control portion 47, the display control portion 46 generates a video signal for displaying the observation image for diagnosis in amounts for a single frame by performing operations to allocate image data of the color component CG for a single field to the B channel of the display apparatus 5, allocate image data of the color component CRS for a single field to the G channel of the display apparatus 5, and allocate image data of the color component CRL for a single field to the R channel of the display apparatus 5, and outputs the generated video signal to the display apparatus 5. Further, if a selection is made to display an observation image for treatment in the deep-part blood vessel observation mode, in response to the control by the control portion 47, the display control portion 46 generates a video signal for displaying the observation image for treatment in amounts for a single frame by performing operations to allocate image data of the color component CBL for a single field to the B channel of the display apparatus 5, allocate image data of the color component CRS for a single field to the G channel of the display apparatus 5, and allocate image data of the color component CRL for a single field to the R channel of the display apparatus 5, and outputs the generated video signal to the display apparatus 5.

Note that the present modification is not limited to a configuration in which operations are performed for displaying only either one of the observation image for diagnosis and the observation image for treatment on the display apparatus 5, and for example a configuration may be adopted so that operations are performed for collectively displaying both of the observation image for diagnosis and the observation image for treatment on the display apparatus 5.

Further, the display control portion 46 of the present modification may be configured to, for example, in a case where a selection is made to display an observation image that is different to each of the observation image for diagnosis and the observation image for treatment in the deep-part blood vessel observation mode, generate a video signal for displaying the relevant observation image in amounts for a single frame by performing signal processing for emphasizing blood vessels with respect to image data of the color components CRS and CRL and performing operations to allocate either one of image data of the color component CBL for a single field and image data of the color component CG for a single field to the B channel and G channel of the display apparatus 5, respectively, and allocate image data to the R channel of the display apparatus 5 using the image data of the color components CRS and CRL on which the signal processing was performed. Note that, in the case of performing the foregoing operations, the image data to be allocated to the R channel of the display apparatus 5 may be any one piece of image data among the pieces of image data of the color components CRS and CRL on which the aforementioned signal processing was performed, or may be image data obtained by addition or averaging of the pieces of image data of the color components CRS and CRL on which the signal processing was performed.

As described above, according to the present modification, in a case where the deep-part blood vessel observation mode is selected, color separation processing using the color separation matrix MG is performed during the illumination period PG in which the return light LG that is in accordance with the illumination pattern IP4 is emitted from the object, and color separation processing using the color separation matrix MH is performed during the illumination period PH in which the return light LH that is in accordance with the illumination pattern IP4 is emitted from the object. Therefore, according to the present modification, in the deep-part blood vessel observation mode, since appropriate color separation that is in accordance with periodic changes in a combination of a plurality of wavelength bands included in return light that is emitted from the object can be performed, the image quality of an observation image that is displayed on the display apparatus 5 can be improved.

Note that the light source apparatus 3 used in the embodiment and respective modifications described above need not have the configuration described above as long as the light source apparatus 3 can emit light of K (3≤K) wavelength bands that are mutually different, and can supply illuminating light including a plurality of wavelength bands among the K wavelength bands for each of N illumination periods in a time-division illumination pattern.

Further, according to the embodiment and respective modifications described above, for example, in a case where the scope memory 24 is not provided in the endoscope 2 or in a case where spectral sensitivity characteristics of the image pickup device 21*b* cannot be identified based on endoscope information stored in the scope memory 24 or the like, a configuration may be adopted so as to illuminate an object using a time-division illumination pattern that is set in advance and to switch a plurality of color separation matrixes that are used in color separation processing of the color separation processing portion 43 in accordance with the relevant time-division illumination pattern.

Further, according to the embodiment and respective modifications described above, for example, in a case where information indicating the model and/or ID number of the endoscope 2 is included in the endoscope information stored in the scope memory 24, a configuration may be adopted so as to set a time-division illumination pattern based on the information and to read in color separation matrixes corresponding to the relevant illumination pattern from the memory 47a.

Furthermore, according to the embodiment and respective modifications described above, for example, endoscope information that includes information indicating a time-division illumination pattern that is set in advance in accordance with the spectral sensitivity characteristics of the image pickup device 21b, and information indicating T color separation matrixes that is set in advance to correspond, respectively, to combinations of a plurality of wavelength bands included in return light emitted from an object that is illuminated using the illumination pattern may be stored in the scope memory 24. Note that, in this case, the number T of color separation matrixes stored in the scope memory 24 is equal to a number N of illumination periods included in a single cycle of the time-division illumination pattern.

Further, according to the embodiment and respective modifications described above, for example, as long as a plurality of wavelength bands are included in return light emitted from the object, a combination of a plurality of wavelength bands included in illuminating light supplied from the light source apparatus 3 may be changed as appropriate for each illumination period of the time-division illumination pattern.

Furthermore, according to the embodiment and respective modifications described above, for example, the accuracy of color separation processing at the color separation processing portion 43 can be improved by setting wavelength bands of the illuminating light so that a plurality of wavelength bands included in return light emitted from the object do not overlap with each other with respect to each illumination period of the time-division illumination pattern.

Further, the embodiment and respective modifications described above are not limited to a configuration in which an illumination pattern is set that adopts two illumination periods as the illumination periods for a single cycle, and for example a configuration may be adopted in which an illumination pattern is set that adopts three or more illumination periods as the illumination periods for a single cycle.

Further, by appropriately changing at least a part of the embodiment and respective modifications described above, for example the present embodiment can also be applied in a case where complementary color filters formed by disposing minute color filters of cyan, magenta, yellow and green in a mosaic shape in a predetermined array at positions corresponding to the respective pixels of the image pickup device 21b are provided instead of the primary color filter 21f.

It should be understood that the present invention is not limited to the embodiment and respective modifications described above, and naturally various changes and applications are possible without departing from the gist of the invention.

What is claimed is:
1. A biological observation system comprising:
a light source apparatus configured to, as illuminating light for illuminating an object, supply a first red light having a wavelength band belonging to a red region and light having a wavelength band belonging to a region other than the red region as a first illuminating light, and supply a second red light having a wavelength band belonging to the red region and having an absorption coefficient for blood that is lower than an absorption coefficient for blood of the first red light, and light having a wavelength band belonging to a region other than the red region as a second illuminating light, and to supply the first illuminating light and the second illuminating light at mutually different timings while switching between the first illuminating light and the second illuminating light;
an image pickup device comprising a plurality of pixels having spectral sensitivities such that a sensitivity to any one color among a predetermined plurality of colors is relatively higher than a sensitivity to other colors than the one color, and which is configured to receive light from an object and generate an image pickup signal for each of the plurality of pixels; and
a processor comprising hardware, wherein the processor is configured to:
perform color separation processing for separating, from an image pickup signal generated by the image pickup device, an image pickup signal corresponding to a color component obtained when an image of light of a predetermined wavelength band included in light from the object is picked up by a pixel having a greatest sensitivity to the light of the predetermined wavelength band among the plurality of pixels; and
in a case where an image pickup signal that is inputted to the processor is an image pickup signal corresponding to the first illuminating light, perform a first color separation processing that separates the image pickup signal into a signal corresponding to the first red light and a signal corresponding to light belonging to a region other than the red region, and in a case where an image pickup signal that is further inputted to the processor is an image pickup signal corresponding to the second illuminating light, switch to a second color separation processing that separates the image pickup signal into a signal corresponding to the second red light and a signal corresponding to light belonging to a region other than the red region,
wherein as light belonging to a region other than the red region, the light source apparatus supplies at least one light among a first blue light, a second blue light having an absorption coefficient for blood that is lower than an absorption coefficient for blood of the first blue light, and a green light,
wherein the image pickup device comprises:
a first pixel having a spectral sensitivity such that, among three colors of red, green and blue, a sensitivity to red is relatively higher than a sensitivity to colors other than red;
a second pixel having a spectral sensitivity such that, among the three colors, a sensitivity to green is relatively higher than a sensitivity to colors other than green; and
a third pixel having a spectral sensitivity such that, among the three colors, a sensitivity to blue is relatively higher than a sensitivity to colors other than blue, wherein the light source apparatus is configured to supply the first blue light, the second blue light, the green light, the first red light and the second red light, and to supply the first red light and the second blue light as the first illuminating light and to supply the second red light and the second blue light as the second illuminating light, and wherein the processor is configured to cause processing for separating, from an image pickup signal generated by the image pickup device, a red color component obtained by picking up an image of the first red light that is included in light from the object at the first pixel, and a blue color component obtained by picking up an image of the second blue light that is included in light from the object at the third pixel to be performed as the first color separation processing, and to cause processing for separating, from an image pickup signal generated by the image pickup device, a red color component obtained by picking up an image of the second red light that is included in light from the object at the first pixel, and a blue color component obtained by picking up an image of the second blue light that is included in light from the object at the third pixel to be performed as the second color separation processing.

2. The biological observation system according to claim 1, wherein the processor is configured to perform operations to add two blue color components obtained by the first color separation processing and the second color separation processing and allocate a resulting color component to a blue channel of a display apparatus, allocate a red color component obtained by the first color separation processing to a green channel of the display apparatus, and allocate a red color component obtained by the second color separation processing to a red channel of the display apparatus.

3. The biological observation system according to claim 1, wherein the processor is configured to perform operations to allocate an average between two blue color components obtained by the first color separation processing and the second color separation processing to a blue channel of a display apparatus, allocate a red color component obtained by the first color separation processing to a green channel of the display apparatus, and allocate a red color component obtained by the second color separation processing to a red channel of the display apparatus.

4. The biological observation system according to claim 1, wherein the processor is configured to perform operations to allocate a blue color component obtained by the first color separation processing to a blue channel of a display apparatus, allocate a red color component obtained by the first color separation processing to a green channel of the display apparatus, and allocate a red color component obtained by the second color separation processing to a red channel of the display apparatus.

5. The biological observation system according to claim 1, wherein the processor is configured to perform signal processing for emphasizing a blood vessel included in the object with respect to two red color components obtained by the first color separation processing and the second color separation processing, and also to perform operations to allocate at least one of two blue color components obtained by the first color separation processing and the second color separation processing or a result of an operation between the two blue color components to each of a blue channel and a green channel of a display apparatus, and to perform operations to allocate at least one of two red color components subjected to the signal processing or a result of an operation between the two red color components to a red channel of the display apparatus.

6. A biological observation system comprising:

a light source apparatus configured to, as illuminating light for illuminating an object, supply a first red light having a wavelength band belonging to a red region and light having a wavelength band belonging to a region other than the red region as a first illuminating light, and supply a second red light having a wavelength band belonging to the red region and having an absorption coefficient for blood that is lower than an absorption coefficient for blood of the first red light, and light having a wavelength band belonging to a region other than the red region as a second illuminating light, and to supply the first illuminating light and the second illuminating light at mutually different timings while switching between the first illuminating light and the second illuminating light;

an image pickup device comprising a plurality of pixels having spectral sensitivities such that a sensitivity to any one color among a predetermined plurality of colors is relatively higher than a sensitivity to other colors than the one color, and which is configured to receive light from an object and generate an image pickup signal for each of the plurality of pixels; and a processor comprising hardware, wherein the processor is configured to:

perform color separation processing for separating, from an image pickup signal generated by the image pickup device, an image pickup signal corresponding to a color component obtained when an image of light of a predetermined wavelength band included in light from the object is picked up by a pixel having a greatest sensitivity to the light of the predetermined wavelength band among the plurality of pixels; and in a case where an image pickup signal that is inputted to the processor is an image pickup signal corresponding to the first illuminating light, perform a first color separation processing that separates the image pickup signal into a signal corresponding to the first red light and a signal corresponding to light belonging to a region other than the red region, and in a case where an image pickup signal that is further inputted to the processor is an image pickup signal corresponding to the second illuminating light, switch to a second color separation processing that separates the image pickup signal into a signal corresponding to the second red light and a signal corresponding to light belonging to a region other than the red region, wherein as light belonging to a region other than the red region, the light source apparatus supplies at least one light among a first blue light, a second blue light having an absorption coefficient for blood that is lower than an absorption coefficient for blood of the first blue light, and a green light, wherein the image pickup device comprises:
   a first pixel having a spectral sensitivity such that, among three colors of red, green and blue, a sensitivity to red is relatively higher than a sensitivity to colors other than red;
   a second pixel having a spectral sensitivity such that, among the three colors, a sensitivity to green is relatively higher than a sensitivity to colors other than green; and
   a third pixel having a spectral sensitivity such that, among the three colors, a sensitivity to blue is relatively higher than a sensitivity to colors other than blue,
wherein the light source apparatus is configured to supply the first blue light, the second blue light, the green light, the first red light and the second red light, and supply the first red light and the second blue light as the first illuminating light and supply the second red light and the green light as the second illuminating light, and
wherein the processor is configured to cause a first color separation processing for separating, from an image pickup signal generated by the image pickup device, a red color component obtained by picking up an image of the first red light that is included in light from the object at the first pixel, and a blue color component obtained by picking up an image of the second blue light that is included in light from the object at the third pixel to be performed, and to cause a second color separation processing for separating, from an image pickup signal generated by the image pickup device, a red color component obtained by picking up an image of the second red light that is included in light from the object at the first pixel, and a green color component obtained by picking up an image of the green light that is included in light from the object at the second pixel to be performed.

7. The biological observation system according to claim 6,
   wherein the processor is configured to perform operations to allocate either one of a blue color component obtained by the first color separation processing and a green color component obtained by the second color separation processing to a blue channel of a display apparatus, allocate a red color component obtained by the first color separation processing to a green channel of the display apparatus, and allocate a red color component obtained by the second color separation processing to a red channel of the display apparatus.

8. A biological observation system comprising:
   a light source apparatus configured to, as illuminating light for illuminating an object, supply a first red light having a wavelength band belonging to a red region and light having a wavelength band belonging to a region other than the red region as a first illuminating light, and supply a second red light having a wavelength band belonging to the red region and having an absorption coefficient for blood that is lower than an absorption coefficient for blood of the first red light, and light having a wavelength band belonging to a region other than the red region as a second illuminating light, and to supply the first illuminating light and the second illuminating light at mutually different timings while switching between the first illuminating light and the second illuminating light;
   an image pickup device comprising a plurality of pixels having spectral sensitivities such that a sensitivity to any one color among a predetermined plurality of colors is relatively higher than a sensitivity to other colors than the one color, and which is configured to receive light from an object and generate an image pickup signal for each of the plurality of pixels; and
   a processor comprising hardware, wherein the processor is configured to:
      perform color separation processing for separating, from an image pickup signal generated by the image pickup device, an image pickup signal corresponding to a color component obtained when an image of light of a predetermined wavelength band included in light from the object is picked up by a pixel having a greatest sensitivity to the light of the predetermined wavelength band among the plurality of pixels; and
      in a case where an image pickup signal that is inputted to the processor is an image pickup signal corresponding to the first illuminating light, perform a first color separation processing that separates the image pickup signal into a signal corresponding to the first red light and a signal corresponding to light belonging to a region other than the red region, and in a case where an image pickup signal that is further inputted to the processor is an image pickup signal corresponding to the second illuminating light, switch to a second color separation processing that separates the image pickup signal into a signal corresponding to the second red light and a signal corresponding to light belonging to a region other than the red region,
   wherein as light belonging to a region other than the red region, the light source apparatus supplies at least one light among a first blue light, a second blue light having an absorption coefficient for blood that is lower than an absorption coefficient for blood of the first blue light, and a green light,
   wherein the image pickup device comprises:
      a first pixel having a spectral sensitivity such that, among three colors of red, green and blue, a sensitivity to red is relatively higher than a sensitivity to colors other than red;
      a second pixel having a spectral sensitivity such that, among the three colors, a sensitivity to green is relatively higher than a sensitivity to colors other than green; and
      a third pixel having a spectral sensitivity such that, among the three colors, a sensitivity to blue is relatively higher than a sensitivity to colors other than blue,
   wherein the light source apparatus is configured to supply the first red light and the second blue light as the first illuminating light, and to supply the second red light, the first blue light and the green light as the second illuminating light, and
   wherein the processor is configured to cause processing for separating, from an image pickup signal generated by the image pickup device, a color component obtained by picking up an image of the first red light that is included in light from the object at the first pixel, and a color component obtained by picking up an image of the second blue light that is included in light from the object at the third pixel to be performed as the first color separation processing, and to cause processing for separating, from an image pickup signal generated by the image pickup device, a color component obtained by picking up an image of the second red light that is included in light from the object at the first pixel, a color component obtained by picking up an image of the green light that is included in light from the object at the second pixel, and a color component obtained by picking up an image of the first blue light that is included in light from the object at the third pixel to be performed as the second color separation processing.

* * * * *